United States Patent [19]

Sussman

[11] Patent Number: 5,067,195
[45] Date of Patent: Nov. 26, 1991

[54] DEVICE FOR CLEANING DENTAL IMPLANT POSTS

[76] Inventor: Harold I. Sussman, 64 Popham Rd., Scarsdale, N.Y. 10583

[21] Appl. No.: 553,974

[22] Filed: Jul. 16, 1990

Related U.S. Application Data

[63] Continuation-in-part of Ser. No. 302,025, Jan. 25, 1989, Pat. No. 4,941,227.

[51] Int. Cl.$^5$ ............................................. D46B 9/04
[52] U.S. Cl. .................... 15/167.001; 15/167.2; 15/160; 15/206; 15/207; 300/21
[58] Field of Search ................. 15/167.1, 167.2, 160, 15/164, 206, 207; 300/21

[56] References Cited

U.S. PATENT DOCUMENTS

| | | | |
|---|---|---|---|
| 887,181 | 5/1908 | Barnes | 15/167.2 |
| 2,066,241 | 12/1936 | Trattner et al. | 15/167.2 |
| 2,077,392 | 4/1937 | Boyd | 15/167.2 |
| 2,214,407 | 9/1940 | Deutsch | 15/167.2 |
| 2,237,694 | 4/1941 | Altstadt | 15/167.2 |
| 2,244,615 | 6/1941 | Garcin | 15/167.2 |
| 2,588,601 | 3/1952 | Zayagno | 15/167.2 |
| 2,771,624 | 11/1956 | Ripper | 15/167.2 |
| 4,131,967 | 1/1979 | Northemann et al. | 15/167.2 |
| 4,137,593 | 2/1979 | Porper | 15/167.2 |
| 4,449,266 | 5/1984 | Northemann et al. | 15/167.2 |
| 4,876,157 | 10/1987 | Barman | 15/167.2 |

*Primary Examiner*—Frankie L. Stinson
*Attorney, Agent, or Firm*—Frishauf, Holtz, Goodman & Woodward

[57] ABSTRACT

A device for cleaning dental implant posts, includes a handle for grasping the device; and a brush secured to one end of the handle. The brush includes (i) a first flexible, springy resilient wire or plastic member secured to the one end of the handle and having a substantially part-circular configuration extending over an arc greater than 90° and less than 180°, the first member having a first inturned free end, (ii) a second flexible, springy resilient wire or plastic member secured to the same end of the handle and having a substantially part-circular configuration extending over an arc greater than 90° and less than 180°, the second member having a second inturned free end in opposing and at least partially facing relation to the first inturned free end so as to define a gap between the first and second inturned free ends which is smaller than the distance between proximal and distal sides of an implant post to be cleaned; and (iii) a plurality of circumferentially arranged bristles secured to each wire or plastic member. The first and second members may be made as a single unitary wire member.

18 Claims, 2 Drawing Sheets

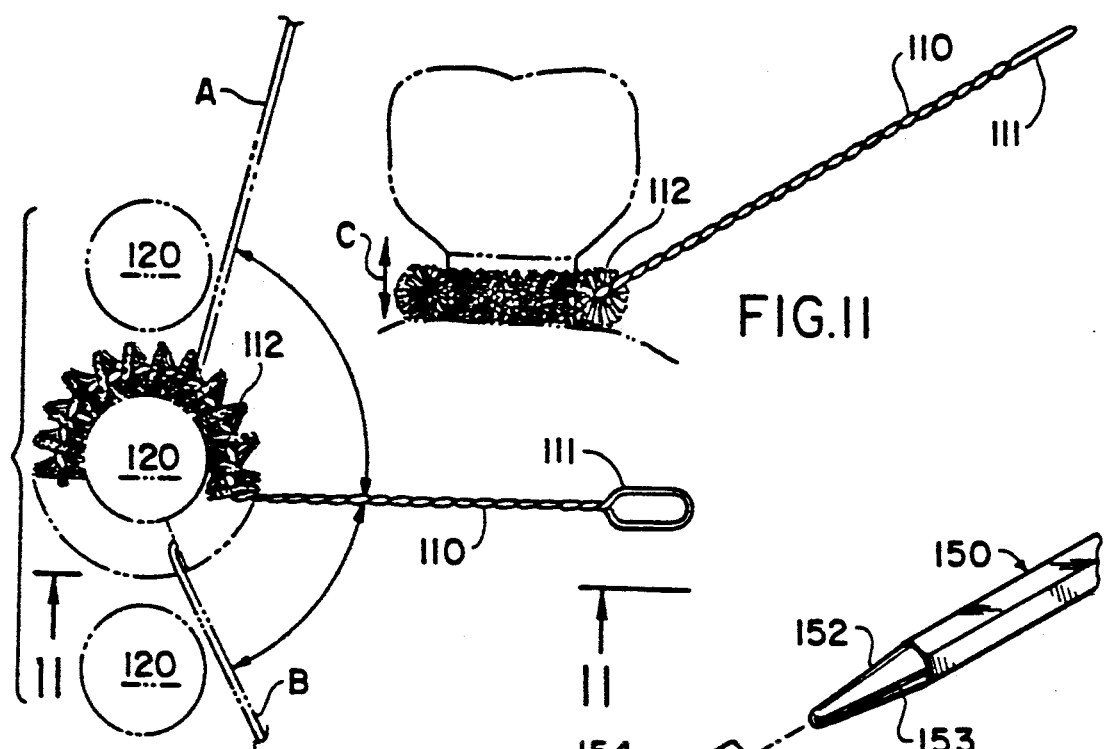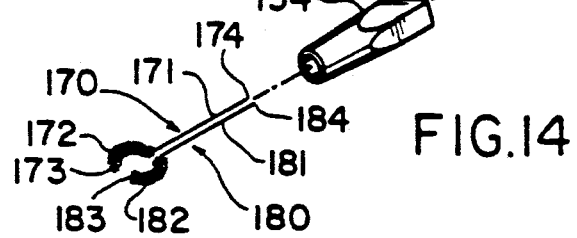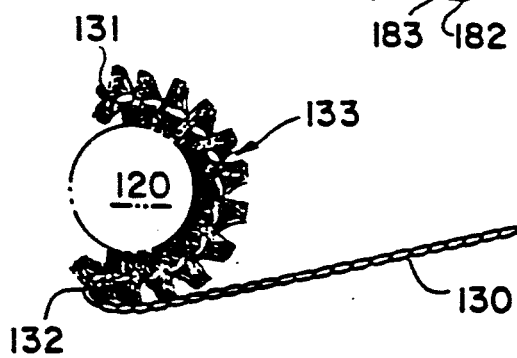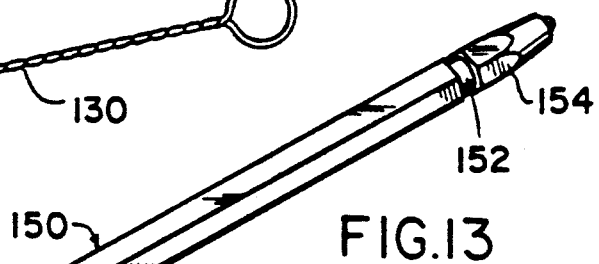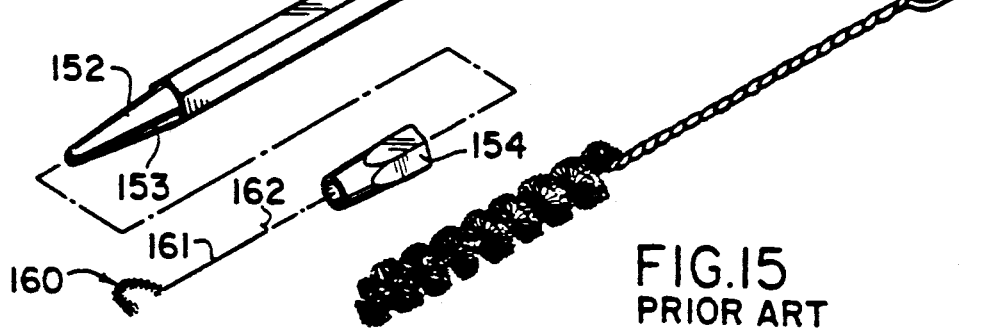

DEVICE FOR CLEANING DENTAL IMPLANT POSTS

CROSS REFERENCE TO RELATED APPLICATION

This application is a continuation-in-part of U.S. Pat. application Ser. No. 07/302,025 filed on Jan. 25, 1989, which will issue into U.S. Pat. No. 4,941,227 on Jul. 17, 1990.

BACKGROUND OF THE INVENTION

This invention relates generally to dental cleaning apparatus, and more particularly, is directed to a device for cleaning dental implant posts.

Surgery to secure dental implants to the jaw bone of a patient has recently become technically and economically available. The use of such dental implants is generally more desirable than so-called "false teeth" which are temporarily adhered to the gum surface. This is because the dental implants are permanently secured in the mouth of the patient.

Generally, surgery for such dental implants starts by making an incision in the gum of the patient to expose the bone over the site of the implant. A special drill then drills into the bone and the implant is screwed into place. The implant is covered for three to sic months to permit undisturbed healing. Thereafter, the top of the implant is exposed and a post is attached. A bridge is then secured on the post and functions in the same manner as a natural tooth.

It will be appreciated that a portion of the post is generally accessible under the bridge. Thus, as with natural—teeth, it is necessary to clean the bridge and post, particularly near and at the gum line. Thorough cleaning at these areas is required to prevent gingival infections around the implant posts, and to prevent plaque from building up in the gum crevice surrounding the implant posts.

Various types of tooth cleaning brushes have been proposed. Most of such brushes provide a single wire element or the like having bristles thereon which are adapted to clean the extremities of the teeth and enter the interproximal areas between teeth. Brushes of this type are shown, for example, in U.S. Pat. Nos. 3,559,226; 3,720,975; 3,939,520; 4,053,959; 4,222,143; and 4,319,377; 4,387,479. However, with these brushes, only one side of a tooth can be cleaned at any given time. In other words, the proximal, distal, buccal and lingual sides of the tooth must be cleaned separately. This requires a relatively large amount of time, and accordingly, the user may not take the time to carefully clean all of the tooth surfaces. Further, with such brushes, it would be difficult to use the same to clean all exposed surfaces of an implant post, particularly toward the lingual side. In addition, there is a tendency for a single pronged straight brush to bend away from the mesial and distal midpoint interproximal surfaces, thereby making cleaning even more difficult.

U.S. Pat. No. 3,677,264 discloses a toothbrush having two parallel and rotatable, generally conically shaped tooth and gum engaging implements. However, it is clear that this toothbrush could not be used to clean the proximal and distal sides of a tooth, let alone an implant post.

In the art of general brushing and scrubbing implements, devices are known having parallel wire elements with bristles thereon. Examples of such devices are shown in U.S. Pat. Nos. 1,195,190 and 1,337,819; British Patent No. 24,259; French Patent Nos. 117,317 and 704,414; and Swedish Patent No. 8,281. In the first place, these devices are not intended for the cleaning of teeth and could not be used as such. Further, the use of parallel wire elements would not enable a person to clean the lingual side of an implant post, along with the remaining sides, in a single cleaning motion.

Although French Patent No. 117, 317 does disclose the use of one wire element being bent at its free end, it is noted that this Patent only envisions the use of one wire element at a time, the other wire element being removed from the device. In any event, a complete cleaning of an implant post could not be achieved in a single motion with this device.

Finally, French patent No. 24,259, although disclosing various bent wires, provides that the free ends of the wires are always parallel or slightly bent outwardly away from each other. Accordingly, complete cleaning of all implant post (or tooth) surfaces with a single motion could not be achieved with this brush.

OBJECTS OF THE INVENTION

It is an object of the present invention to provide a device for cleaning dental implant posts that overcomes the problems in the prior art and which is easy and economical to manufacture.

It is another object of the present invention to provide a device for cleaning dental implant posts in which all post surfaces can be cleaned with a single cleaning motion.

It is still another object of the present invention to provide a device for cleaning dental implant posts in which lingual, buccal, proximal and distal sides of an implant post can be cleaned with a single cleaning motion.

It is still another object of the present invention to provide a brush specifically designed for cleaning the neck of the implant post and keratinizing (toughening the outer tissue layer of the gum) the gingival crevice to make the area more resistant to infection, and to deplaque the entire circumference of the implant post while requiring access from only one side of the post.

It is yet another object of the present invention to provide a device for cleaning dental implant posts that can be made on existing manufacturing equipment, using existing and/or readily available manufacturing techniques, so that the resulting article is easy and economical to manufacture.

The above and other objects, features and advantages of the present invention will become readily apparent from the following detailed description which is to be read in connection with the accompanying drawings.

SUMMARY OF THE INVENTION

A device for cleaning dental implant posts comprises a handle for manually grasping said device; and brushing means secured to one end portion of the handle. The brushing means includes a flexible, resilient, spring-like brush member connected to said one end of said handle means and having a generally semicircular or U-shaped configuration, said generally semicircular or U-shaped configuration defining a receiving space therein for receiving an implant post to be cleaned and resiliently surrounding a major portion of the received implant post, said brush member having first and second free ends at the ends of said generally semicircular or U- shaped configuration which are in opposing and in at least partially facing relation to each other so as to define a gap between said first and second free ends for insertion of an implant post to be cleaned through said gap between said free ends and into said receiving space. The brushing means further includes a plurality of bristles secured to said brush member, said bristles at least being directed inwardly and downwardly of said generally semicircular or U-shaped configuration. The inwardly directed bristles extend into said receiving space for engaging an implant post received in said receiving space over substantially the complete extent of said generally semicircular or U-shaped configuration so as to simultaneously brush a major portion of the received implant post. The downwardly directed bristles engage gum tissue for keratinizing the outer layer of the engaged tissue.

Also disclosed is a method for making the cleaning device of the present invention.

BRIEF DESCRIPTION OF THE DRAWINGS

FIG. 10 is a plan view showing an embodiment of the invention formed of a single wire brush member having the end portion thereof bent into a generally U-shape which extends at an angle to the handle portion thereof;

FIG. 11 is a side elevational view as per line 11—11 taken in FIG. 10;

FIG. 12 is a plan view, similar to FIG. 10, showing a similar embodiment as FIG. 10 but having re-entrant end portions;

FIG. 13 is a perspective view of a conventional handle-type brush holder, with some parts shown in spaced relation, for holding a brush according to the present invention, the brush being removably and replaceably mounted in the reusable brush holder;

FIG. 14 shows a modified embodiment using two cooperating brush members mounted in a single handle member; and FIG. 15 shows a conventional straight brush from which the brush of the present invention can be made.

DETAILED DESCRIPTION

Figure 1:
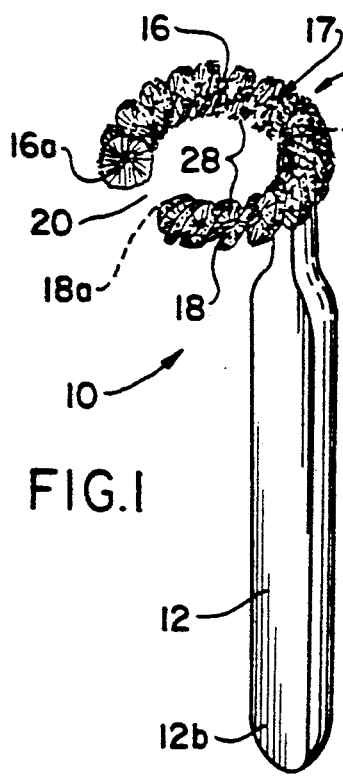
FIG. 1 is a perspective view of a device for cleaning dental implant posts according to the present invention.

Referring to the drawings, a device 10 according to one embodiment of the present invention for cleaning dental implant screws or posts (hereinafter generally referred to as "post") includes an elongated handle 12 with which a person can grasp device 10. A brush member 14 is secured to one end 12a of handle 12 by means of adhesive or any other suitable securing means, while the user grasps the opposite end 12b of handle 12.

Figure 3:
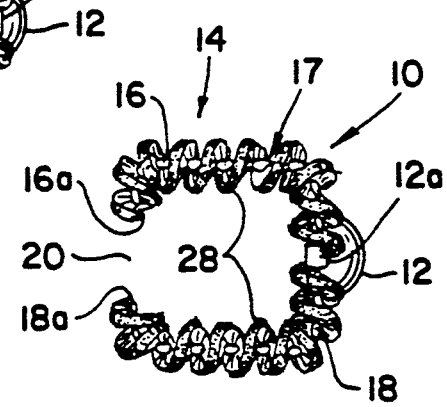
FIG. 3 is a top plan view of a device according to another embodiment of the present invention.
Figure 4:
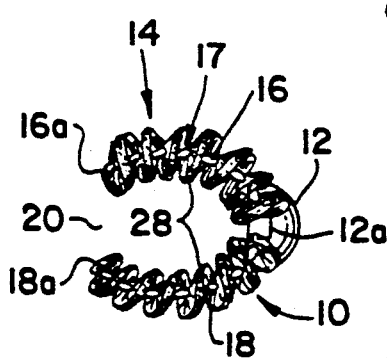
FIG. 4 is a top plan view of a device according to yet another embodiment of the present invention.

Brush member 14 includes first and second flexible, resilient, springy, wire members 16 and 18 secured to end 12a of handle 12, wire members 16, 18 each having a convex configuration. In this regard, each of the wire members 16, 18 can have a substantially part-circular configuration extending over an arc greater than 90° and less than 180°, as shown in FIG. 1. Alternatively, wire members 16, 18 can each have a substantially U-shaped configuration, as shown in FIG. 3 or a generally oval shape as shown in FIG. 4. Other suitable shapes could be used. In any case, first wire member 16 has a first inturned or inwardly directed free end 16a, and second wire member 18 has a second inturned or inwardly directed free end 18a.

In the embodiments of FIGS. 1, 3 and 4, it is preferable that wire members 16 and 18 be formed from a single, continuous, integral wire member 17 extending over an arc greater than 180°.

Figure 5:
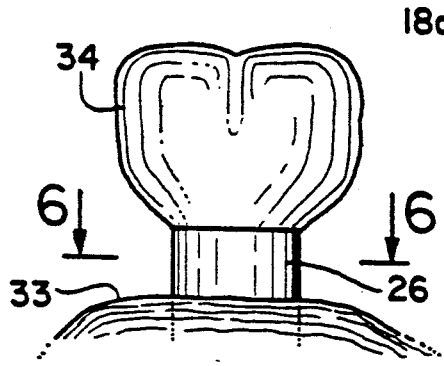
FIG. 5 is a side elevational view of a side of a tooth implant with post with which the present invention is used.

It will be appreciated that because first and second wire members 16 and 18 have mirror image convex configurations, the second inturned or inwardly directed free end 18a of wire portion 18 is in opposing and at least partially facing relation to first inturned free end 16a of wire portion 16 so as to define a gap 20 therebetween. The size of gap 20 is smaller than the distance between proximal and distal sides 22 and 24 (see FIGS. 5 and 6) of an implant post 26 to be cleaned.

Further, brush member 14 includes a plurality of bristles 28 secured to each wire member 16 and 18. The brush member 14 can be a twisted wire brush, such as shown in U.S. Pat. Nos. 3,559,226 or 4,319,377, for example. Although it is only necessary from the standpoint of the present invention to provide inwardly directed bristles 28, it is preferable that bristles 28 extend circumferentially around each wire member 16 and 18 at any point thereon. In this manner, the gingival surface and adjacent tooth surfaces will also be cleaned.

Figure 6:
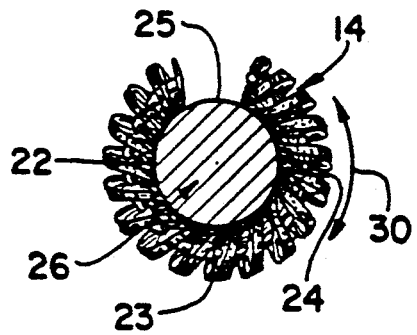
FIG. 6 is a cross-sectional view, along line 6—6 of FIG. 5, showing the device of FIG. 1 used to clean the post 26.
Figure 7:
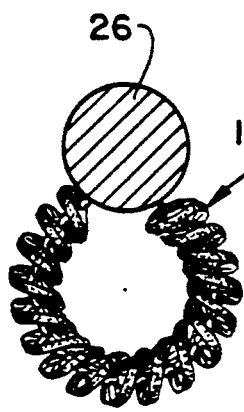
FIG. 7 is a cross-sectional view of the post of FIG. 5, showing the start of operation of the device of FIG. 1 for wrapping around the implant post.

In use, as shown in FIG. 7, and with respect to the embodiment of FIG. 1, inturned ends 16a and 18a are moved into contact with the buccal side 23 of a post 26. Upon application of a force toward the lingual side 25 of post 26, wire members 16 and 18 are resiliently forced apart and around post 26 and "spring" back to the position shown in FIG. 6. Thereafter, all surfaces of post 26 are cleaned by moving brush member 14 only a small amount in the direction of double-headed arrow 30.

Figure 8:
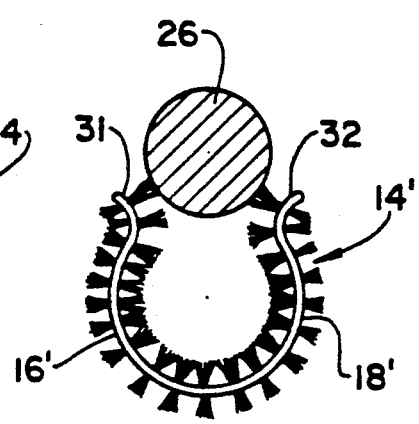
FIG. 8 shows a modified device of the present invention.

As shown in FIG. 8, the brush member 14', formed of members 16', 18', may be provided with outwardly turned free ends 31, 32 which serve as "camming" surfaces to facilitate sliding of the brush member 14 over the post 26. The free end portions 31, 32 may have bristles 28 thereon, or may be free of bristles, as desired. The modified device of FIG. 8 is shown as being made of plastic material, instead of wire members such as twisted wire members, to show an alternate embodiment. Also, when the brush member 14' is made of plastic material, the camming surfaces 31, 32 may more easily slide over the post 26. The plastic material from which the brush member 14 is made can be any of the biologically safe springy plastic materials, such as polyethylene, polypropylene, or other suitable materials.

It will be appreciated that, with all of the embodiments of the invention, complete cleaning of all exposed surfaces of implant post 26 occurs with a single insertion of the post into the opening between the wire (or plastic) cleaning members, and with a single rotating or reciprocating cleaning motion over only a small angle in the direction of arrow 30 in FIG. 6. At the same time, gingival surface 33, the underside of tooth 34 and any adjacent tooth surfaces are also cleaned.

An important feature of the present invention is the spring action provided by the resilient wire or plastic members 16, 18. By virtue of the spring action provided by members 16, 18, the device effectively has a "memory" so that when the members 16, 18 are forced apart or deformed when passing around post 26, the member 16, 18 spring back to their initial positions to effectively wrap at least partly around the post 26 so as to provide excellent cleaning characteristics without the necessity of inserting the device from the lingual side.

Figure 9:
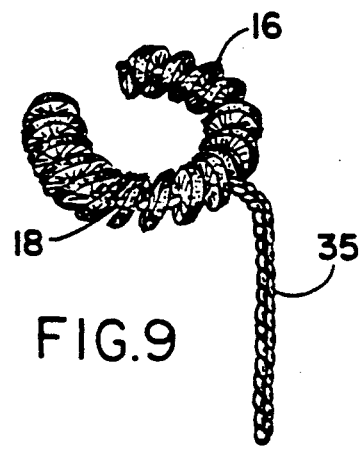
FIG. 9 shows a perspective view of a further modified device of the present invention.

The wire or plastic members 16, 18 may be integrally formed as a single member. Instead of the single unitary member adhered to the handle 12 in the manner shown in FIGS. 1-4, the members 16, 18 can have a connection member 35 extending therefrom, as shown in FIG. 9, and the elongated connecting member 35 may be connected to a handle member in a manner similar to that shown in any one of U.S. Pat. Nos. 4,387,479; 4,319,377; or 4,222,143; or in any other suitable manner. The connection member 30 is made of the same material (i.e., wire or plastic) as member 16, 18. Additionally, bristles are connected to the wire (i.e. twisted wire) member in the same manner as is known in the art, for example as shown by the above-mentioned patents, or as shown in U.S. Pat. No. 3,5559,226, for example, or are embedded in plastic members 16, 18.

While the members 16, 18 were described above as being made of wire, preferably twisted wire with bristles thereon, they could be fabricated of any other suitable material, such as plastic material, having the bristle portions embedded therein or otherwise attached thereto. When made of plastic material, the material should be biologically safe for use in the mouth, and should have the necessary resiliency and spring characteristics so as to provide the springy action described hereinabove.

Figure 2:
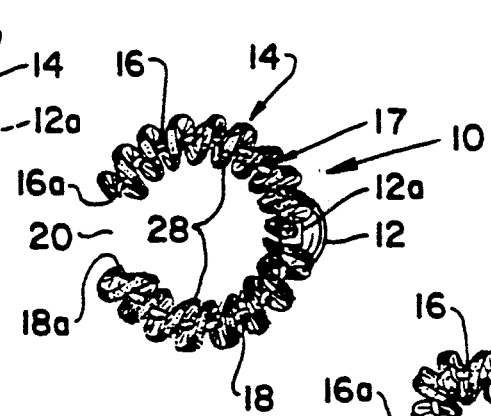
FIG. 2 is a top plan view of the device of FIG. 1.

In a preferred embodiment, the implant screws or posts which are to be cleaned are generally around 4 mm, and range generally from between about 3.5 to about 4.5 mm in diameter. Preferably, the gap 20 is about 2.5 mm, and when the device is generally circular as shown in FIG. 2, the inner diameter of the circle (from wire-to-wire) should be about 4 mm or slightly less so as to provide a tight fit. If the bristles 28 are sufficiently stiff, the inner diameter of the "circle" formed by the members 16, 18 (FIG. 2) may be slightly larger than 4 mm, and the bristles will still give sufficient brushing against the rod or post to provide proper cleaning.

When the device is attached to a handle in the manner shown, for example, in U.S. Pat. Nos. 4,22,143; 4,319,377; or 4,387,479, the handle may be re-used and the wire member portion 14 can be made as a replaceable unit.

Referring to FIGS. 10 and 11, an embodiment of the invention includes a twisted wire handle member 110 having a loop 111 at the end portion thereof. The loop 111 is optional, and could instead be straight. The twisted wire handle has at its distal end portion a brush portion 112 formed on the twisted wire member in a conventional manner. Initially, the distal end brush portion 112 is formed as a straight brush as shown in FIG. 15, as is conventional, for example manufactured by E-Z Floss, Palm Springs, Calif. As can be seen from FIG. 10, the handle and support portion for the brush is made of twisted wire. Preferably, the brush of the present invention utilizes twisted wire of 0.020 inches diameter, to provide sufficient stiffness while also providing sufficient resilience. After formation of the conventional brush, the distal brush end 112 is bent or otherwise formed in a generally U-shape or generally semicircular shape as shown in FIG. 10 by means of a bending machine or the like. The generally U-shape or semicircular shape of portion 112 is preferably at approximately right angles to the longitudinal axis of handle portion 110, as seen in FIG. 10. FIG. 10 illustrates the use of the brush with implant posts 120. FIG. 10 shows, for example, three adjacent posts, the brush of the present invention being mounted around the center post 120. In use, the general U-shaped or semicircular shaped brush portion 112 is placed around a post, as shown, to engage a major portion of the circumference of a post 120, and the cleaning tool is swung over an arc from position A to position B, or vice versa. The brush may be swung several times, back and forth, through said arc in order to clean most of the exposed peripheral surfaces of the post 120 about which it is mounted. If a large swinging arc is permitted, due to restraint of adjacent teeth, posts, etc., almost all of the post can be cleaned by one insertion and by swinging between points A and B. If a portion of the post remains uncleaned, the cleaning tool of the present invention can be removed from the tooth, flipped over by 180°, placed over the other side of the post, and swung again over the arc from A to B, and back and forth, as required. As used herein, the term "major portion" describes engaging the brush over about 180° (or more) of the circumference of the post 120 when the brush is placed on the post. Preferably, the brush resiliently engages or resiliently "snaps over" the post 120 to engage more than 180° so that it positively stays in place during use, without inadvertently slipping off the post.

The brush may also be lifted up and down in the direction of arrow C shown in FIG. 11 to provide a vertical brushing motion relative to the post, to enhance cleaning of the post 120 and to also clean the gingival area, the gum crevice surrounding the implant post and the underside of the artificial tooth mounted on the post 120.

The advantage of the embodiment of FIGS. 10 and 11 is that a conventional brush having a straight brush portion can be easily bent and modified to take the form of the present invention as illustrated in FIGS. 10 and 11. Only a simple bending technique is required after formation and manufacture of the basic straight brush, thereby greatly lowering the cost of manufacture and making manufacture thereof relatively simple.

FIG. 12 shows a modified embodiment wherein the end portions of the U-shaped or generally semicircular shaped brush are re-entrant. This means that U-shape or the semicircle defined by the brush is greater than 180°.

The embodiment of FIG. 12 can be manufactured by a simple bending technique from a conventional straight brush, as described above with respect to FIG. 10. In the embodiment of FIG. 12, the generally semicircular shaped brush portion is bent back further by around an additional 90° as compared to the embodiment of FIG. 10. In some applications, this arrangement is advantageous. For example, since the embodiment of FIG. 12 has re-entrant ends 131, 132, the additional leverage provided by the orientation of the handle 130 in FIG. 12 will make it easier to "snap" the resilient brush portion 133 over the post. Since the ends 131, 132 are re-entrant slightly, a small amount of resilient yielding of the brush portion 133 may be required to mount the brush over the post. After mounting, the brush of FIG. 12 is swung over the arc as illustrated with respect to FIG. 10 to provide brushing of the post, as well as the gum and tooth areas. The brush of FIG. 12 can be moved up and down in the direction of arrow C of FIG. 11, to provide improved brushing effects.

FIG. 13 illustrates an embodiment of the invention for use in connection with a reusable handle member, such as the E-Z HANDLE ® manufactured by E-Z Floss, Palm Springs, Calif. The handle shown in FIG. 13 comprises an elongated body member 150 having a tapered end portion 152 with an anchor slot 153 therein. A collet 154 having a tapered inner surface is slidably mounted over the tapered portion 152 and is frictionally locked thereon. The brush of the present invention, designated as item 160 in FIG. 13, has an elongated portion 161 (similar to handle 110, 130), with a bent handle-engaging portion 162 (optional) at the remote end thereof. In use, the elongated portion 161 is mounted into the anchor slot 153 with the bent portion 162 received in the slot for engagement purposes. Then, the collet is slid thereover to lock same into the anchor slot. The bent end 162 can instead be made straight, in which case it will still fit in the anchor slot 153. The user, can, if desired, make the bend 162 by hand.

The brush 160 of the present invention has a generally U-shaped or generally semicircular working brush portion, similar in shape to either the embodiment of FIG. 10 or the embodiment of FIG. 12. The only difference between the embodiments of FIGS. 10 and/or 12 is that the loop 111 at the end of the handle portion (see FIG. 10) is eliminated, and the end portion of the "handle" of the brush is bent inwardly (as shown by 162 in FIG. 14) to engage an anchor slot in the handle 150. The apparatus of FIG. 14 is used in the same manner as the apparatus of FIG. 10 or FIG. 12. After the brush becomes worn or if the brush breaks, the collet 154 is removed (slid off), and a new brush member is inserted to "renew" the cleaning device.

The handle 150 of FIG. 13 has mounting portions 152 and associated collets 154 at both opposite ends thereof. Therefore, two brushes of the present invention can be mounted at opposite ends of the device, or one brush of the present invention can be mounted at one end, and a conventional cleaning device can be mounted at the other end, as desired.

As shown in FIG. 14, a device similar to the embodiment of FIGS. 1 and 9 can be fabricated using two brush members 170, 180, each of which is similar to the brush member 160 of FIG. 13, except for the shape of the brush portion at the brush-end thereof, as will be explained below. The brush members 170, 180 each have respective twisted wire handle or handle engaging portions 171, 181, and also respectively have brush end portions 172, 182, respectively. The brush end portions 172, 182 cooperate to define a brush end similar to that shown in FIGS. 1-4 and/or 6-9. The brush members 170, 180 are preferably used with the handle 150 of FIG. 13. In use, the brush members are placed adjacent each other, substantially as shown in FIG. 14, and are inserted through the elongated opening of the collet 154. The handle portions 171, 181 are then placed in the anchor slot 153 of the handle 150, and the collet is slid thereover to frictionally engage tapered portion 152 to essentially lock the two brush members 170, 180 in place, with their brush portions 172, 182 oriented in the position shown in FIG. 14. The tip ends 173, 183 of the brush members 170, 180 can be inwardly directed (that is, re-entrant) as shown in FIGS. 1-4 and 6-9, and/or as shown in FIGS. 10, 12 and 13. The brush of FIG. 14 is used in the same manner as the other brushes of the present invention.

It should be clear that all of the brushes of all of the figures could extend around substantially 180° or more of a generally circular or generally U-shape, it being preferred that the brush extends more than 180° to engage a larger extent of an engaged post. The wire or other material from which the brushes are made is preferably of resilient wire so that better engagement and retention on the post is achieved.

In the embodiment of FIG. 14, the ends 174, 184 of the respective brushes 170, 180 can be straight (as shown) or bent over in the same manner as bent portion 162 of FIG. 13, as desired. If the end portions are straight, they can be bent over (similar to bent portion 162) by the user (by hand) just prior to mounting in the anchor slot 153 of the handle 150.

An advantage of the devices of FIGS. 10-14 is that they are easily and economically manufactured using presently available brush making techniques for making straight brushes. After the straight brush is made, or during the manufacturing process for the straight brush, the end portion can be bent in a generally U-shaped or generally semicircular shape, as shown in FIG. 10-14, to produce the brush of the present invention in a simple, economical manner, while using presently existing manufacturing equipment and techniques, and without requiring new, expensive manufacturing machinery. Thus, the present invention, as illustrated in FIGS. 10-14, can be quickly and readily brought to market to benefit the public.

Having described specific preferred embodiments of the invention with reference to the accompanying drawings, it will be appreciated that the present invention is not limited to those precise embodiments, and that various changes and modifications may be effected therein by one of ordinary skill in the art without departing from the scope or spirit of the invention as defined in the appended claims.

What is claimed is:

1. A device for cleaning dental implant posts, said cleaning device comprising:

handle means for manually grasping said device; and
brushing means secured to one end portion of said handle means, said brushing means including:

i) a flexible, resilient, spring-like brush member means connected to said one end of said handle means and having a generally semicircular or U-shaped configuration, said generally semicircular or U-shaped configuration defining a receiving space therein for receiving an implant post to be cleaned and resiliently surrounding a major portion of the periphery of the received implant post, said brush member means having first and second free ends at the ends of said generally semicircular or U-shaped configuration which are in opposing and in at least partially facing relation to each other so as to define a gap between said first and second free ends for insertion of an implant post to be cleaned through said gap between said free ends and into said receiving space; and ii) a plurality of bristles secured to said brush member means, said bristles at least being directed inwardly and downwardly of said generally semicircular or U-shaped configuration, said inwardly directed bristles extending into said receiving space for engaging an implant post received in said receiving space over substantially the complete extent of said generally semicircular or U-shaped configuration so as to simultaneously brush a major portion of the periphery of the received implant post; and said downwardly directed bristles engaging gum tissue adjacent the implant post for keratinizing the outer layer of the engaged tissue;

said flexible, resilient, spring-like brush member means with said plurality of bristles secured thereto being dimensioned so as to be receivable between adjacent teeth at least at the gingival area, and being arranged to brush a dental implant post supporting a tooth at the lingual surface of said post, at the buccal surface of said post, and at the gingival margin adjacent said post, said brush member means and said bristles together engaging around said received post over said major portion of the periphery of said post; said brush member means being resiliently deflectable or spreadable apart when passed between teeth and over a post to engage over said major portion of the received post.

2. The device of claim 1, wherein said bristles further comprise upwardly directed bristles, whereby said brushing means is reversible to brush not only said implant post, but also said gum tissue for keratinizing the outer layer of the engaged tissue.

3. The device of claim 1, wherein said handle means comprises a twisted wire member means, and wherein said brush member comprises a continuation of said twisted wire member with said bristles thereon.

4. The device of claim 3, wherein said generally semicircular or U-shaped configuration is formed by bending said brush member means relative to said handle means.

5. The device of claim 4, wherein said receiving space opens through said gap in a direction substantially perpendicular to said handle means.

6. The device of claim 4, wherein said generally semicircular configuration defines said receiving space which opens in a direction substantially parallel to said handle means.

7. The device of claim 1, wherein said brush member means of said brushing means comprises first and second brush members, each brush member having an elongated portion and a bent portion, said bent portions being arranged adjacent each other so as to cooperatively define said generally semicircular or U-shaped configuration, and said elongated portions being mounted adjacent each other so as to fix said bent portions in said cooperative relation.

8. The device of claim 7, wherein said handle means comprises an elongated slot for receiving said elongated members of said first and second brush members, and locking means for locking said elongated members in said elongated slot.

9. The device of claim 1, wherein said brush member means of said brushing means comprises an elongated member coupled to said generally semicircular or U-shaped configuration; and wherein said handle means comprises an elongated member having an elongated slot therein for receiving said elongated member of said brushing means, and means for locking said elongated member of said brushing means in said elongated slot of said handle.

10. The device of claim 9, wherein said brushing means is removably secured in said handle means.

11. The device of claim 1, wherein said generally semicircular or U-shaped configuration extends over an arc greater than 90° and less than 180°.

12. The device of claim 1, wherein said generally semicircular or U-shaped configuration extends over an arc greater than 180° and less than 360°.

13. The device of claim 1, wherein said brush member means and said bristles together engage around said received post over an arc of at least about 180°.

14. A method for making a device for cleaning dental implant posts, said cleaning device comprising:

handle means for manually grasping said device; and
brushing means secured to one end portion of said handle means, said brushing means including:
  i) a flexible, resilient, spring-like brush member connected to said one end of said handle means and having a generally semicircular or U-shaped configuration, said generally semicircular or U-shaped configuration defining a receiving space therein for receiving an implant post to be cleaned and resiliently surrounding a major portion of the periphery of the received implant post, said brush member having first and second free ends at the ends of said generally semicircular or U-shaped configuration which are in opposing and in at least partially facing relation to each other so as to define a gap between said first and second free ends for insertion of an implant post to be cleaned through said gap between said free ends and into said receiving space; and
  ii) a plurality of bristles secured to said brush member, said bristles at least being directed inwardly of said generally semicircular or U-shaped configuration so as to extend into said receiving space for engaging an implant post received in said receiving space over substantially the complete extent of said generally semicircular or U-shaped configuration so as to simultaneously brush a major portion of the periphery of the received implant post;

the method comprising:
forming an elongated brush having a twisted wire support member having bristles connected thereto at a brush end thereof, and being free of bristles at another end, said end being free of bristles comprising a handle portion; and
bending said brush end generally in a U-shaped or semicircular shape to form said generally semicircular or U-shaped brush configuration;
said flexible, resilient, spring-like brush member means with said plurality of bristles secured thereto being dimensioned so as to be received between adjacent teeth at least at the gingival area, and being arranged and formed to brush a dental implant post supporting a tooth at the lingual surface of said post, at the buccal surface of said post, both opposite side portions of said post, and at the gingival margin adjacent said post, said brush member means and said bristles together engaging around said received post over said major portion of the periphery of said post; said brush member means being resiliently deflectable or spreadable apart when passed between teeth and over a post to engage over said major portion of the received post.

15. The method of claim 14, wherein said brush end is bent such that said receiving space opens through said gap in a direction substantially perpendicular to said handle portion.

16. The method of claim 14, wherein said brush end is bent such that said receiving space opens through said gap in a direction substantially parallel to said handle portion.

17. The method of claim 16, wherein said receiving space opens so as to face toward a distal end of said handle portion.

18. The method of claim 14, wherein said brush member and said bristles are formed so that together they engage around said received post over an arc of at least about 180°.

* * * * *